(12) United States Patent
Niland et al.

(10) Patent No.: US 10,426,911 B2
(45) Date of Patent: Oct. 1, 2019

(54) RESPIRATORY THERAPY CONDENSATION ADAPTOR

(71) Applicant: Vapotherm, Inc., Exeter, NH (US)

(72) Inventors: William F. Niland, Arnold, MD (US); Felino V. Cortez, Jr., Bowie, MD (US)

(73) Assignee: VAPOTHERM, INC., Exeter, NH (US)

( * ) Notice: Subject to any disclaimer, the term of this patent is extended or adjusted under 35 U.S.C. 154(b) by 1181 days.

(21) Appl. No.: 14/455,478

(22) Filed: Aug. 8, 2014

(65) Prior Publication Data

US 2015/0040895 A1    Feb. 12, 2015

Related U.S. Application Data

(60) Provisional application No. 61/863,610, filed on Aug. 8, 2013.

(51) Int. Cl.
*A61M 16/00* (2006.01)
*A61M 16/08* (2006.01)
(Continued)

(52) U.S. Cl.
CPC .... *A61M 16/0816* (2013.01); *A61M 16/0057* (2013.01); *A61M 16/0463* (2013.01);
(Continued)

(58) Field of Classification Search
CPC .............. A61M 16/0833; A61M 16/04; A61M 16/0465; A61M 16/0816; A61M 16/1045;
(Continued)

(56) References Cited

U.S. PATENT DOCUMENTS 3,670,965 A    6/1972 Marand
3,864,326 A    2/1975 Babington
(Continued)

FOREIGN PATENT DOCUMENTS

RU      2009111135 A    10/2010
WO   WO 2012160477 A1 *  11/2012 ........ A61M 16/0816

OTHER PUBLICATIONS

International Search Report and Written Opinion for PCT/US2014050382 dated Nov. 28, 2014.
(Continued)

*Primary Examiner* — Tan-Uyen T Ho
*Assistant Examiner* — Victoria Murphy
(74) *Attorney, Agent, or Firm* — White & Case LLP

(57) ABSTRACT

Systems, devices, and methods for coupling a tracheostomy tube to a source of humidified breathing gas are disclosed. An adaptor includes a housing, a tracheostomy tube connection device, and a baffle. The housing has an interior surface, an exterior surface, and a breathing gas port. The tracheostomy tube connection device is positioned within the housing and includes an input port for receiving a flow of humidified breathing gas from the breathing gas port and an output port for coupling with the tracheostomy tube. The tracheostomy tube connection device has an internal surface defining a breathing gas passage and an external surface spaced from the interior surface of the housing to create a condensation passage. The baffle may be positioned between the breathing gas port and the input port to cause controlled condensation from the flow of humidified breathing gas by disrupting the flow of humidified breathing gas.

25 Claims, 8 Drawing Sheets

(51) Int. Cl.
*A61M 16/04* (2006.01)
*A61M 16/16* (2006.01)
*A61M 16/10* (2006.01)

(52) U.S. Cl.
CPC .... *A61M 16/0465* (2013.01); *A61M 16/0497* (2013.01); *A61M 16/0808* (2013.01); *A61M 16/0875* (2013.01); *A61M 16/10* (2013.01); *A61M 16/16* (2013.01); *A61M 2202/0208* (2013.01); *A61M 2206/14* (2013.01)

(58) Field of Classification Search
CPC .. A61M 16/20; A61M 16/08; A61M 16/0808; A61M 16/0875
See application file for complete search history.

(56) References Cited

U.S. PATENT DOCUMENTS

| | | | |
|---|---|---|---|
| 3,949,743 A | 4/1976 | Shanbrom | |
| 4,007,737 A * | 2/1977 | Paluch | A61M 16/06 128/201.13 |
| 4,094,317 A | 6/1978 | Wasnich | |
| 4,171,962 A | 10/1979 | Kippel et al. | |
| 4,177,945 A | 12/1979 | Schwartz et al. | |
| 4,333,451 A | 6/1982 | Paluch | |
| 4,520,812 A | 6/1985 | Freitag et al. | |
| 4,558,708 A | 12/1985 | Labuda et al. | |
| 4,620,670 A | 11/1986 | Hughes | |
| 4,819,625 A | 4/1989 | Howe | |
| 4,832,012 A | 5/1989 | Raabe et al. | |
| 4,911,157 A | 3/1990 | Miller | |
| 4,951,661 A | 8/1990 | Sladek | |
| 5,226,411 A | 7/1993 | Levine | |
| 5,461,695 A | 10/1995 | Knoch | |
| 5,630,409 A | 5/1997 | Bono et al. | |
| 5,813,401 A | 9/1998 | Radcliff et al. | |
| 6,166,025 A | 12/2000 | Harding et al. | |
| 6,718,969 B1 | 4/2004 | Rubin et al. | |
| 8,915,245 B2 | 12/2014 | Cortez, Jr. et al. | |
| 2003/0150445 A1 | 8/2003 | Power et al. | |
| 2004/0069307 A1 | 4/2004 | Rich et al. | |
| 2004/0237178 A1 | 12/2004 | Landeros | |
| 2005/0061318 A1 | 3/2005 | Faram | |
| 2006/0219243 A1 | 10/2006 | Walstrom | |
| 2007/0128912 A1 * | 6/2007 | Glaze | F16L 13/142 439/320 |
| 2008/0000470 A1 | 1/2008 | Minocchieri et al. | |
| 2009/0062855 A1 | 3/2009 | Lemery et al. | |
| 2010/0071693 A1 | 3/2010 | Allum et al. | |
| 2010/0089395 A1 | 4/2010 | Power et al. | |
| 2010/0154797 A1 * | 6/2010 | Landis | A61M 16/0463 128/205.27 |
| 2010/0258114 A1 | 10/2010 | Cortez, Jr. et al. | |
| 2012/0085343 A1 * | 4/2012 | Cortez | A61M 11/02 128/200.14 |
| 2012/0272954 A1 | 11/2012 | Landis et al. | |
| 2013/0081616 A1 * | 4/2013 | Tatkov | A61M 16/04 128/201.13 |
| 2013/0133645 A1 | 5/2013 | Lee et al. | |

OTHER PUBLICATIONS

International Search Report and Written Opinion for PCT/US2013/022692 dated Jul. 29, 2014.
Supplementary European Search Report, Application No. EP 14 83 4470, dated Apr. 26, 2017.

* cited by examiner

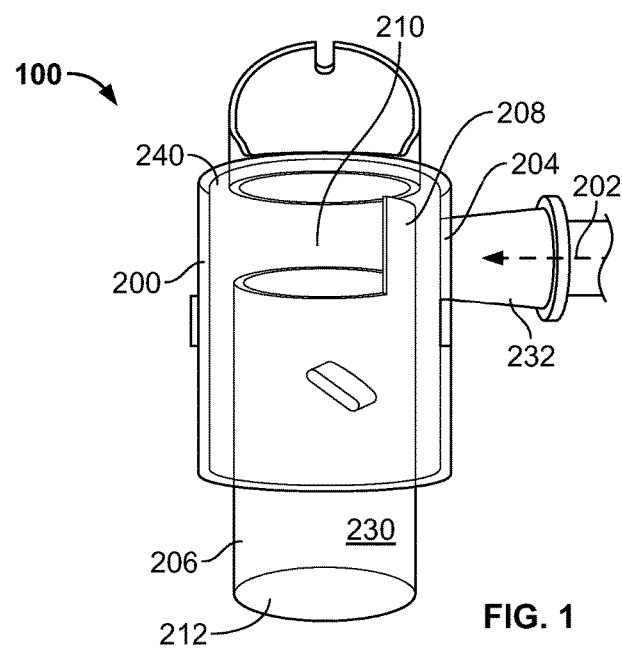
FIG. 1
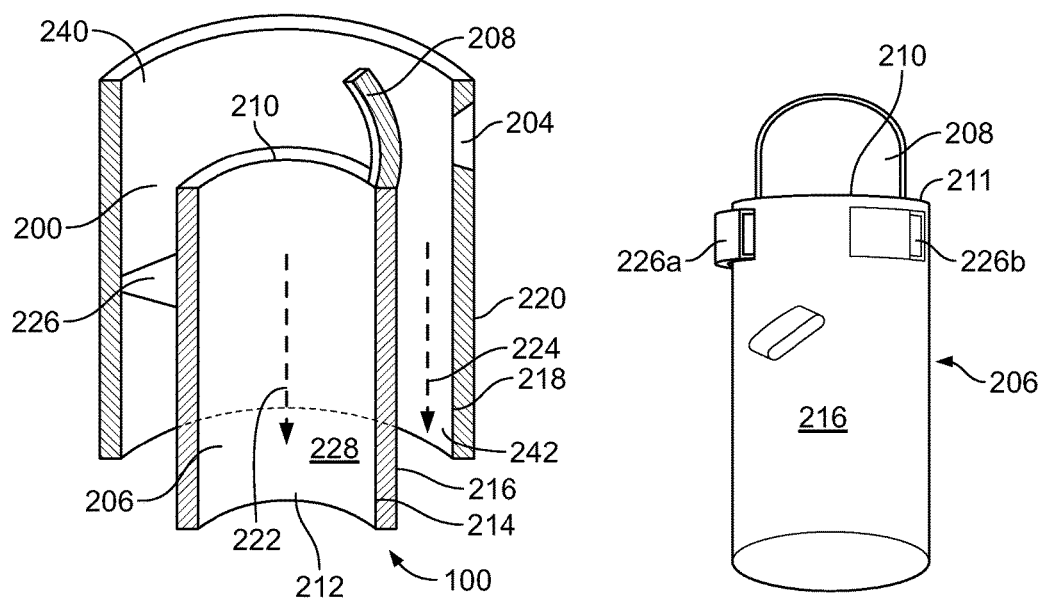
FIG. 2
FIG. 3

RESPIRATORY THERAPY CONDENSATION ADAPTOR

CROSS-REFERENCE TO RELATED APPLICATIONS

This application claims the benefit of U.S. Provisional Application No. 61/863,610, filed on Aug. 8, 2013, which is hereby incorporated herein by reference in its entirety.

BACKGROUND

Patients with respiratory ailments may be administered supplemental breathing gases, such as oxygen, for example, to aid in respiration. These breathing gases are typically provided from a breathing gas supply, such as an oxygen tank. A delivery device, such as a nasal cannula, may be coupled to the breathing gas supply and inserted into a patient's nasal passages for delivery of the breathing gas to the patient for inhalation. Alternatively, for patients that have had a tracheostomy, a surgical procedure to create an opening through the neck into the trachea, breathing gas may be supplied directly to the trachea through a tracheostomy tube (also known as a trach tube) that extends from the patient's neck.

During treatments in which the breathing gas is humidified, moisture may condense near the connection of a breathing gas supply tube to the tracheostomy tube. This moisture may drip into the trachea, causing irritation and discomfort. Accordingly, systems, devices, and methods for handling this moisture are desirable.

Furthermore, in a healthy patient, the upper airway warms, cleans, and moistens the air that a patient breathes. However, these mechanisms are bypassed when a patient breathes through a tracheostomy tube. Mucus secretions may accumulate in the tracheostomy tube, impairing proper breathing and potentially causing infection. Accordingly, systems, devices, and methods for clearing mucus from the tracheostomy tube are desirable.

SUMMARY

Disclosed herein are systems, devices, and methods for coupling a tracheostomy tube to a source of humidified breathing gas. In certain implementations, the systems, devices, and methods include a baffle for reducing the entry of condensate from the humidified breathing gas into the tracheostomy tube. The baffle may direct liquid droplets of condensate entrained in the breathing gas into a condensation passage, while allowing the breathing gas to be inhaled by a patient. The adaptor may have an open end which allows air to escape when it is not being inhaled, which may facilitate use of the adaptor with high flow therapy systems.

In one aspect, an adaptor for coupling a tracheostomy tube to a source of humidified breathing gas includes a housing, a tracheostomy tube connection device, and a baffle. The housing may have an interior surface, an exterior surface, and a breathing gas port for receiving a flow of humidified breathing gas from the source that extends from the external surface to the interior surface. The tracheostomy tube connection device may be positioned within the housing and include an input port for receiving the flow of humidified breathing gas from the breathing gas port and an output port for coupling with the tracheostomy tube. In some implementations, the tracheostomy tube connection device has an internal surface defining a breathing gas passage and an external surface spaced from the interior surface of the housing to create a condensation passage. In certain implementations, the baffle is positioned between the breathing gas port and the input port to cause controlled condensation from the flow of humidified breathing gas by disrupting the flow of humidified breathing gas. The baffle may be integrally formed with the tracheostomy tube connection device.

In certain implementations, the exterior surface of the tracheostomy tube connection device includes at least one projection to space the tracheostomy tube connection device from the interior surface of the housing. In some implementations, the interior surface of the housing includes at least one projection to space the tracheostomy tube connection device from the interior surface of the housing. In certain implementations, the adaptor also includes at least one flange attached to the exterior of the tracheostomy tube connection device to prevent displacement of the tracheostomy tube and to distribute force if the tracheostomy tube connection device is moved. The at least one flange may have a surface configured to engage a neck of a patient, the surface having a connector to connect the at least one flange to a tracheostomy band circling the neck. The connector may be a hook or loop connector.

In some implementations, the adaptor also includes at least one flange attached to the exterior of the housing to prevent displacement of the tracheostomy tube and to distribute force if the tracheostomy tube connection device is moved. In certain implementations, the adaptor also includes a supply tube having a first end to receive the flow of humidified breathing gas and a second end coupled to the breathing gas port of the housing. In some implementations, the adaptor also includes a swivel connector coupled to the first end of the supply tube for connection with the source of humidified breathing gas. The breathing gas port may include an elbow connector for coupling with the source of humidified breathing gas. The breathing gas port may include a straight connector for coupling with the source of humidified breathing gas.

In certain implementations, the output port of the tracheostomy tube connection device has an interior surface configured to engage an exterior surface of the tracheostomy tube. The output port of the tracheostomy tube connection device may have an exterior surface configured to engage an interior surface of the tracheostomy tube. In some implementations, the exterior surface of the tracheostomy tube connection device has a first perimeter, and the adaptor also includes a vent cap coupled to the housing, the vent cap including an inner surface having a second perimeter, and the first perimeter is smaller than the second perimeter such that condensate that accumulates on the vent cap flows into the condensation passage. The vent cap may be removably coupled to the housing.

In some implementations, the vent cap includes a cap base for removably coupling with the housing, a sloping planar structure coupled to the cap base to form a first opening and a second opening, the first opening larger than and positioned opposite to the second opening with respect to the second perimeter, and the first opening and the second opening capable of operating as vents for exhaled air. In certain implementations, the adaptor also includes a tube sleeve configured to receive a suction tube to suction away secretions in the airway of a patient. In some implementations, the adaptor also includes a suction tube having a first tube end and a second tube end, the first tube end extending out of the adaptor for coupling with a suctioning apparatus and the second tube end extending into the airway of a patient to suction away secretions when positioned within the tube sleeve. The tube sleeve may be fixedly bonded to a surface of the tracheostomy tube connection device and the second tube end may extend through the tube sleeve so as to be capable of extending into the airway of the patient. The condensation passage may be capable of serving as a vent for exhaled air.

In another aspect, an adaptor for coupling a tracheostomy tube to a source of humidified breathing gas includes an input port configured to receive a flow of humidified breathing gas, a breathing gas passage for coupling with the tracheostomy tube, a condensation passage, and a baffle positioned between the input port and the breathing gas passage to disrupt the flow of humidified breathing gas to cause controlled condensation from the flow of humidified breathing gas into the condensation passage. In yet another aspect, an adaptor for coupling a tracheostomy tube to a source of humidified breathing gas includes a housing having means for receiving a flow of humidified breathing gas from the source, means for connecting the housing to the tracheostomy tube, and means for causing controlled condensation from the flow of humidified breathing gas by disrupting the flow of humidified breathing gas into the housing. The means for causing controlled condensation may be integrally formed with the means for connecting the housing to the tracheostomy tube.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 1 is a perspective view of a tracheostomy tube adaptor device;

FIG. 2 is a fragmentary cross-sectional view of the tracheostomy tube adaptor device of FIG. 1;

FIG. 3 is a perspective view of a tracheostomy tube connection device;

DETAILED DESCRIPTION

Figure 4:
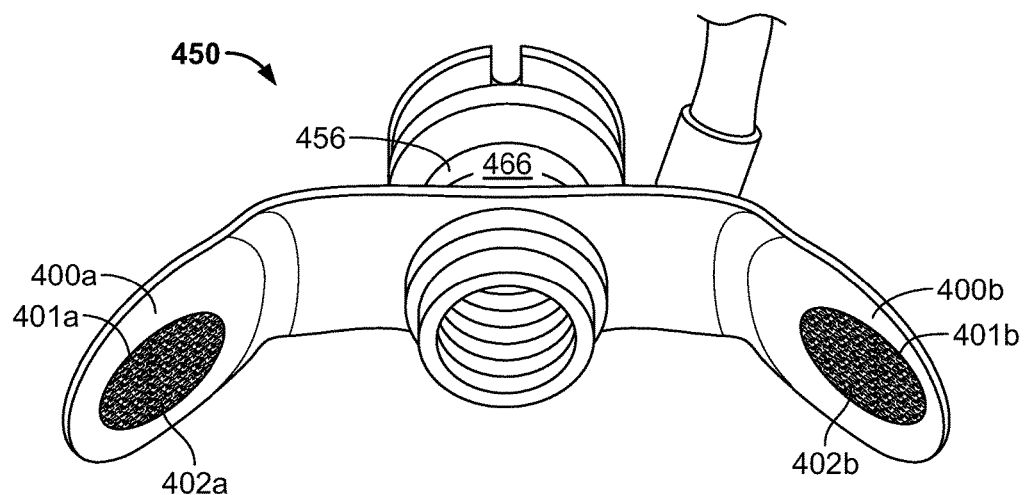
FIG. 4 is a perspective view of a tracheostomy tube adaptor with flanges.

To provide an overall understanding of the systems, devices, and methods described herein, certain illustrative embodiments will be described. Although the embodiments and features described herein are specifically described for use in connection with a high flow therapy system, it will be understood that all the components and other features outlined below may be combined with one another in any suitable manner and may be adapted and applied to other types of respiratory therapy and respiratory therapy devices, including low flow oxygen therapy, continuous positive airway pressure therapy (CPAP), mechanical ventilation, oxygen masks, Venturi masks, any other suitable respiratory therapy or respiratory therapy devices, and any combinations thereof.

The tracheostomy tube adaptor disclosed herein, also referred to as a respiratory therapy condensation device couples a source of humidified breathing gas to the tracheostomy tube of a patient in such a way that condensation is deterred from entering the patient's trachea and causing discomfort. The tracheostomy tube adaptor may deter condensation because it includes a structure (e.g., a baffle) that disrupts the flow of humidified breathing gas before the gas enters the tracheostomy tube of the patient. The structure can deflect liquid droplets entrained in the humidified breathing gas (e.g., due to condensation) and cause the droplets to exit out of a separate passage. Tracheostomy tube adaptors disclosed herein may also be used with a suctioning apparatus for suctioning mucus from a tracheostomy tube of a patient. The tracheostomy adaptors may allow a suction catheter to be inserted into the tracheostomy tube while also supplying breathing gas and ventilation. The adaptors may facilitate switching between ventilation and high flow therapy.

FIG. 1 depicts a tracheostomy tube adaptor device 100, according to certain embodiments. Although the term tracheostomy tube adapter is used, device 100 may also be referred to as a respiratory therapy condensation adaptor. The illustrated adaptor 100 includes a housing 200 and a tracheostomy tube connection device 206 positioned within the housing 200. The housing 200 and the tracheostomy tube connection device 206 may be formed from a non-porous hard plastic or other material suitable for use in breathing devices. Tracheostomy tube connection device 206 has a smaller diameter than housing 200 and is substantially concentric to housing 200. The housing 200 has a breathing gas port 204 for receiving a flow of humidified breathing gas 202. The illustrated breathing gas port 204 includes a connector 232 for coupling the tracheostomy tube adaptor device 100 with a source of humidified breathing gas. Although a straight connector 232 is illustrated, the connector 232 may include other shapes such as an elbow shape depicted in other embodiments herein or any other suitable shape. The housing 200 may be open on its upper end 240, which allows breathing gas to freely exit from the top of the housing 200. In some embodiments, to facilitate the escape of air, upper end 240 faces away from the patient in use. Since the humidified breathing gas is allowed to escape from the housing, excessive pressure does not build up in a patient's airway when gas flow rates exceed the rate of inhalation. Such a design facilitates the use of an adaptor 100 with high flow therapy systems in which breathing gas flow rates can greatly exceed inhalation rates.

The tracheostomy tube connection device 206 within housing 200 has an input port 210 for receiving the flow of humidified breathing gas originating from a source of humidified breathing gas (e.g., source 102 of FIG. 14) and an output port 212 for coupling with the tracheostomy tube of a patient. A baffle 208 is positioned between the input port 210 and the breathing gas port 204 to disrupt the flow of humidified breathing gas from the source. By disrupting the flow of breathing gas, condensation that may occur in the vicinity of the adaptor device 100 or that is entrained in the gas flow can be prevented from entering the airway of a patient and causing irritation.

The illustrated output port 212 of FIG. 1 has an exterior surface 230, which may be configured to engage an interior surface of a tracheostomy tube protruding from the neck of a patient. In some embodiments, an interior surface 228 (shown in FIG. 2) of the output port 212 may be configured to engage an exterior surface of the tracheostomy tube.

FIG. 2 depicts a fragmentary cross-sectional view of the tracheostomy tube adaptor device 100 of FIG. 1, according to certain embodiments. The housing 200 of the adaptor 100 has an interior surface 218 and an exterior surface 220. The breathing gas port 204 extends from the exterior surface 220 to the interior surface 218. The tracheostomy tube connection device 206 positioned within the housing 200 includes an interior surface 214 and an exterior surface 216. The interior surface 214 defines a breathing gas passage 222 through which breathing gas may travel to the airway of a patient through output port 212, which is configured to engage a tracheostomy tube protruding from a neck of a patient. The exterior surface 216 of the device 206 is spaced from the interior surface 218 of the housing to create a condensation passage 224. In some embodiments, the condensation passage 224 may function as a vent to eliminate exhaled gas and prevent build up of pressure in the airway of a patient.

Projection 226, is used to space the device 206 from the housing 200. The projection 226 extends from the exterior surface 216 of the device 206 to engage the interior surface of the housing 200 when the device 206 is positioned within the housing 200. In some embodiments, one or more of the projections may extend from the interior surface 218 of the housing to engage the exterior surface of the device when the device is positioned within the housing. Furthermore, although only one projection 226 is illustrated, additional projections may be used to space the housing 200 from the tracheostomy tube connection device 206. Although the housing 200 and the device 206 are illustrated and described as separate devices herein, they may be formed as a single unitary device.

The illustrated baffle 208 is positioned between the input port 210 of the tracheostomy tube connection device 206 and the breathing gas port 204 to disrupt the flow of humidified breathing gas 202 flowing from the breathing gas port 204. This arrangement can prevent condensation occurring in the vicinity of the adaptor device 100 or condensation entrained in the breathing gas from entering the airway of a patient and can direct condensation into the condensation passage 224. After impacting the baffle 208, condensation may flow towards the bottom end 242 of the condensation passage and exit the tracheostomy tube adaptor 100 entirely.

In some embodiments, entrained liquid droplets are inhibited by the baffle 208 because entrained liquid droplets adhere to the baffle 208 on impact and are carried through the condensation passage 224 by gravitational force acting on the droplets. Although a baffle is shown in FIG. 2, other structures that achieve separation of vapor and liquid by gravitational force and/or surface adhesion may be used to inhibit the flow of condensation into the tracheostomy tube of a patient. For example, in some embodiments, the structure for controlling condensation includes other types of flow-directing vanes or panels, any other suitable structure, or combination thereof.

FIG. 3 depicts the tracheostomy tube connection device 206 of FIG. 2 removed from housing 200, according to certain embodiments. The illustrated device 206 has an attached baffle 208 and an input port 210. The illustrated device 206 has projections 226a and 226b extending from its exterior surface 216 for positioning the device 206 within a housing 200 and creating the condensation passage.

In some embodiments, the baffle 208 has a slightly curved planar body with an arcuate upper edge. The baffle 208 extends above the upper edge 211 of input port 210 and has an area larger than the cross sectional area of the breathing gas port 204 (shown in FIG. 2) so that it can redirect the flow of most or substantially all of the breathing gas (and entrained droplets, if any) exiting breathing gas port 204. The baffle 208 may be formed from a non-porous hard plastic or other material suitable for use in breathing devices. Although the baffle 208 depicted in FIG. 3 is integrally formed in the tracheostomy tube connection device 206, in some embodiments the baffle 208 may be attached using an attachment or bonding mechanism including adhesives, fasteners, snap fits, or welded connections, any other suitable attachment or bonding mechanism, or combination thereof.

FIG. 4 depicts an embodiment of a tracheostomy tube adaptor device 450 having a tracheostomy tube connection device 456. The illustrated device 450 has an exterior surface 466 to which are attached flanges 401a and 401b. Flanges 401a and 401b have surfaces 400a and 400b, respectively, configured to engage a neck of a patient. The illustrated surfaces 400a and 400b further have connectors 402a and 402b, respectively, to connect the flanges 401a and 401b to a tracheostomy band (not shown) circling the neck of the patient. Although the illustrated device 450 depicts two flanges, 401a and 401b, connected to exterior surface 466, any suitable number of flanges 401 may be attached to exterior surface 466. Furthermore, in some embodiments, a flange or flanges 401 extend from an exterior surface 220 of a housing 200. The connectors 402a and 402b may be hook or loop connectors (e.g., Velcro®) for engaging corresponding loop or hook connectors positioned on the tracheostomy band. The flanges 401 enable the device 450 to be secured to the neck of a patient to prevent torque being applied to the tracheostomy tube in the event the device 450, a supply tube 500 (shown in FIG. 5) connected to the device, and/or a gas source are moved.

Figure 5:
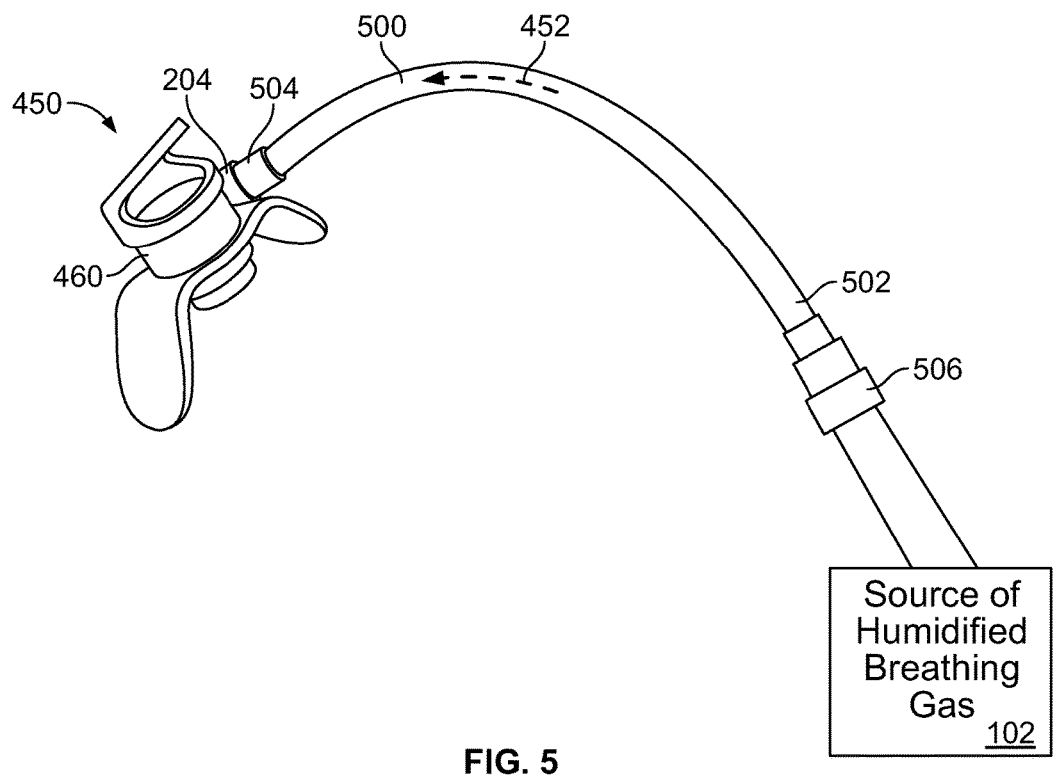
FIG. 5 is a perspective view of a tracheostomy tube adaptor device coupled to a supply tube for connecting a breathing gas port of the adaptor to a flow of humidified breathing gas.
Figure 6:
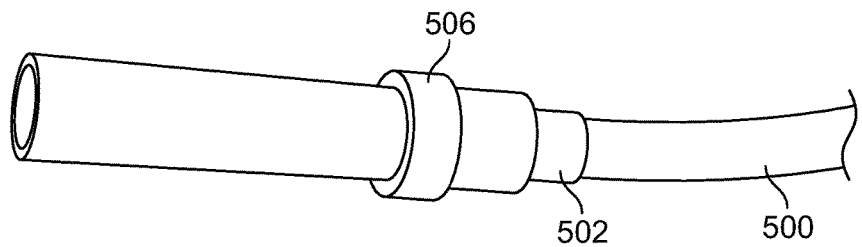
FIG. 6 is a perspective view of a swivel connector coupled to a first end of a supply tube for coupling with a source of humidified breathing gas.

FIG. 5 depicts the tracheostomy tube adaptor device 450 of FIG. 4 having a breathing gas port 454 coupled to a supply tube 500 having a swivel connector 506, according to certain embodiments. FIG. 6 depicts enlarged perspective view of the swivel connector 506 of FIG. 5. The supply tube 500 has a first end 502 to receive the flow of humidified breathing gas 452 and a second end 504 coupled to the breathing gas port 454 of the housing 460. The illustrated first end 502 is coupled to a swivel connector 506 for connection with a source of humidified breathing gas 102. The illustrated swivel connector 506 is coupled to a first end 502 of a supply tube 500. The swivel connector allows rotation between first end 502 and second end 504. By accommodating such rotation, the swivel connector 506 may prevent and/or reduce torque being transferred to the tracheostomy tube via the tube 500 and the tracheostomy tube adaptor device 100 (e.g., due to movement of the source of humidified breathing gas 102).

Figure 7:
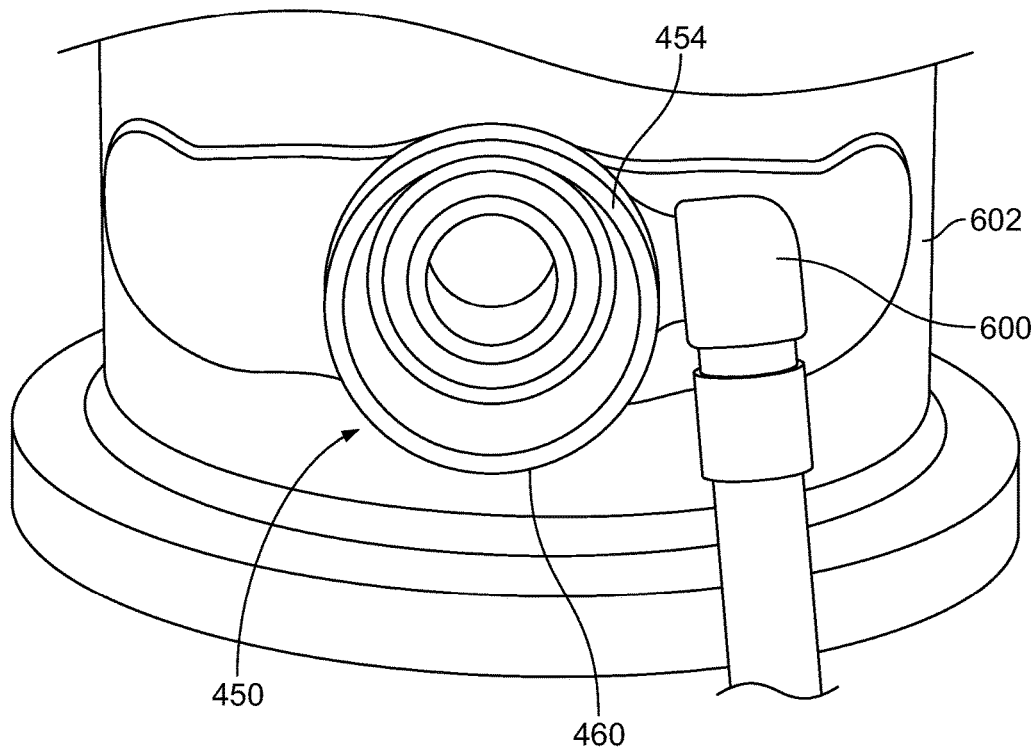
FIG. 7 is a perspective view of an elbow connector for coupling with the source of humidified breathing gas and a tracheostomy band encircling a neck of a patient.

FIG. 7 depicts the tracheostomy tube adaptor device 450 of FIG. 4 having a housing 460, according to certain embodiments. The illustrated housing 460 has a breathing gas port 454 having an elbow connector 600. The illustrated elbow connector 600 couples with a source of humidified breathing gas for transport of humidified breathing gas into the adaptor device 450. The elbow connector 600 allows the tracheostomy tube adaptor device 450 to have a low profile because the supply tubing 500 need not protrude far from the tracheostomy tube adaptor device 450.

Figure 8:
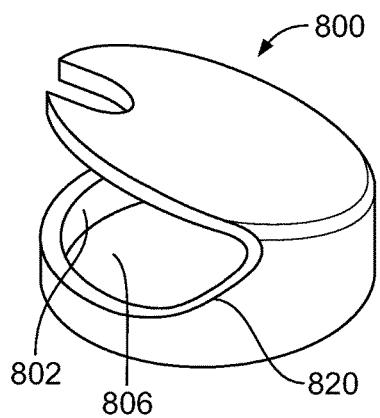
FIG. 8 is a perspective view of a vent cap for coupling with a housing of the tracheostomy tube adaptor device.

FIG. 8 depicts an embodiment of a vent cap 800, according to certain embodiments. The illustrated vent cap 800 has an inner surface 802 and a cap base 820. The cap 800 may be removably coupled to an upper end 240 of the housing 200 of adaptor 100 (shown in FIG. 1). The vent cap 800 may prevent foreign objects from entering a patient's tracheostomy tube. Also, vent cap 800 may prevent the upper end 240 of the tracheostomy tube adaptor 100 (shown in FIG. 1) from becoming obstructed by an object resting against the upper end of the adaptor because air can escape from the first opening 806.

Figure 9:
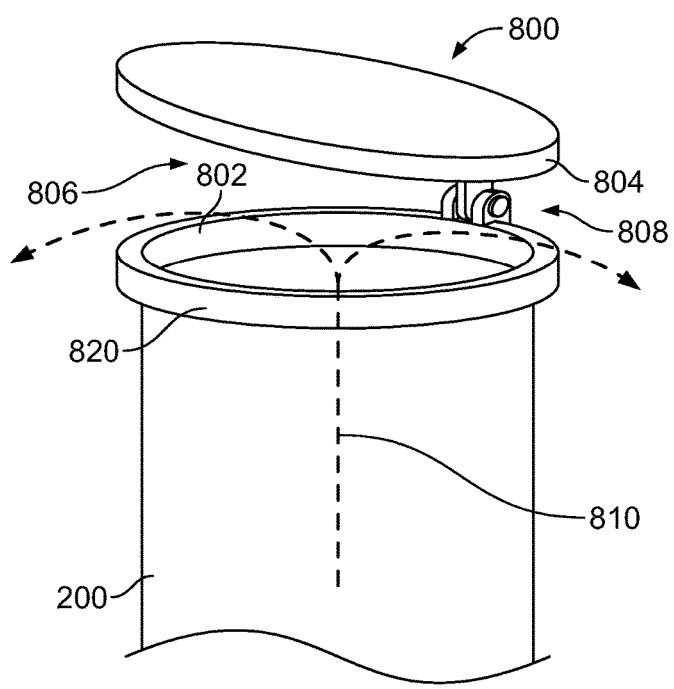
FIG. 9 is a perspective view of a vent cap coupled with a housing of the tracheostomy tube adaptor device.

FIG. 9 depicts an embodiment of a vent cap 800 coupled to upper end 240 of a housing 200, according to certain embodiments. The vent cap 800 has a sloping planar structure 804 coupled to the cap base 820. The orientation of the sloping planar structure 804 with respect to the cap base 820 forms a first opening 806 and a second opening 808. First opening 806 is larger than second opening 808 due to the slope of planar structure 804, and first opening 806 is positioned opposite second opening 808 with respect to the cap base 820. Both first opening 806 and second opening 808 provide vents through which a flow of exhaled gas 810 may pass.

Figure 10:
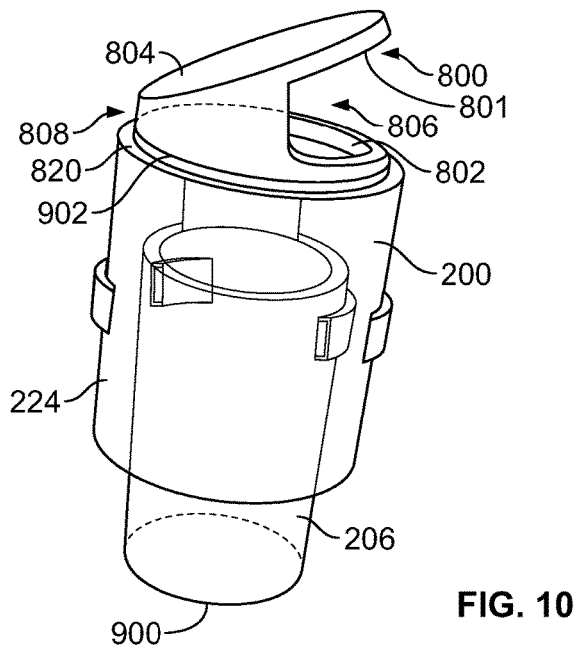
FIG. 10 is a perspective view of a tracheostomy tube adaptor device with the vent cap of FIG. 8 coupled to the housing of the tracheostomy tube adaptor device.

FIG. 10 depicts the tracheostomy tube adaptor device 100 having a housing 200 and a tracheostomy tube connection device 206 positioned within the housing 200, according to certain embodiments. The illustrated tracheostomy tube connection device 206 has an exterior surface 206 having a first perimeter 900. The illustrated housing 200 is coupled to a vent cap 800, which has an inner surface 802. The inner surface 802 has a second perimeter 902, which is larger than the first perimeter 900. This allows condensation that accumulates on the vent cap 800 (e.g. on the bottom surface 801) to flow into a condensation passage 224, which is positioned between first perimeter 900 and second perimeter 902, to prevent the condensation from entering the airway of a patient and causing irritation. Such condensation may instead adhere to the bottom surface 801 of vent cap 800, flow onto the inner surface 802, and exit from the bottom end 242 of the tracheostomy tube adaptor device 100.

Figure 11:
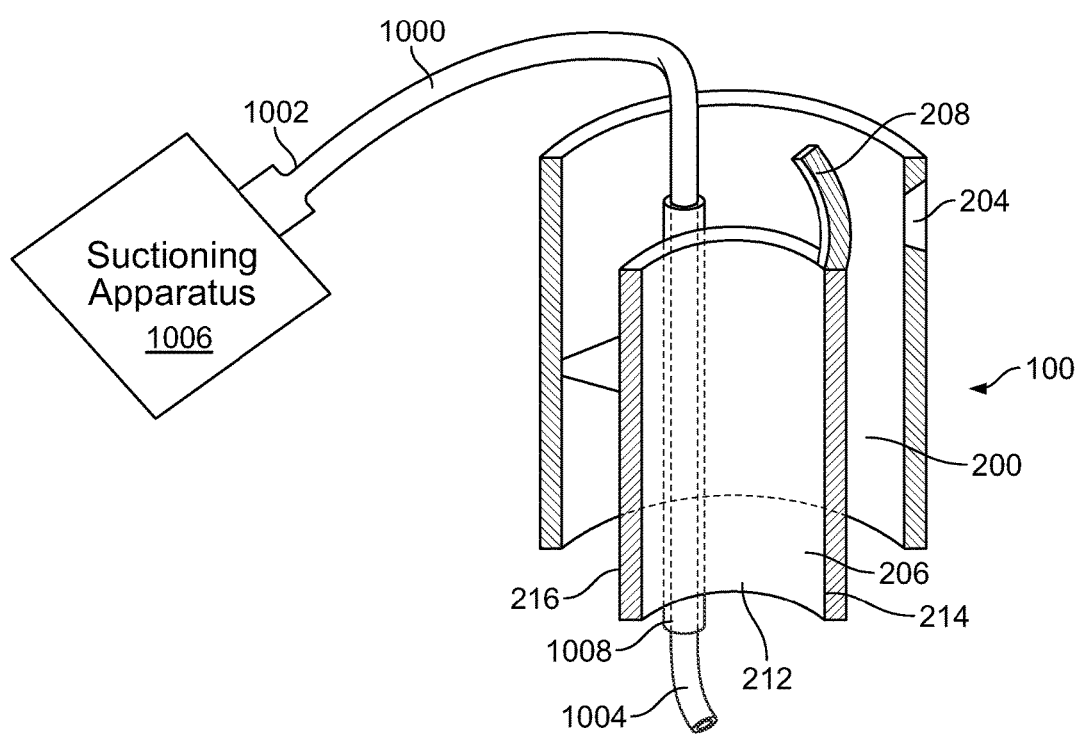
FIG. 11 is a fragmentary cross-sectional view of a tracheostomy tube adaptor device with a suction tube for coupling with a suctioning apparatus and capable of extending into the airway of a patient to suction away secretions.

FIG. 11 depicts a fragmentary cross-sectional view of a tracheostomy tube adaptor device 100, according to certain embodiments, having a suction tube 1000 for a fixed mode of suctioning away secretions in the airway of a patient. The suction tube 1000 has a first tube end 1002 extending out of the adaptor device 100 and coupling with a suctioning apparatus 1006, e.g., via a Luer lock connector. The suction tube 1000 also has a second tube end 1004 capable of extending into the airway of a patient to suction away secretions. A tube sleeve 1008 may be integrally formed into the tracheostomy tube connection device or bonded to an interior or exterior surface of the tracheostomy tube connection device. The suction tube 1000 may be inserted into the tube sleeve 1008 to prevent multiple insertion points of the suction tube 1000 into the airway of the patient, which could cause irritation, and to provide easy access to the airway of a patient for suctioning away secretions.

Figure 12:
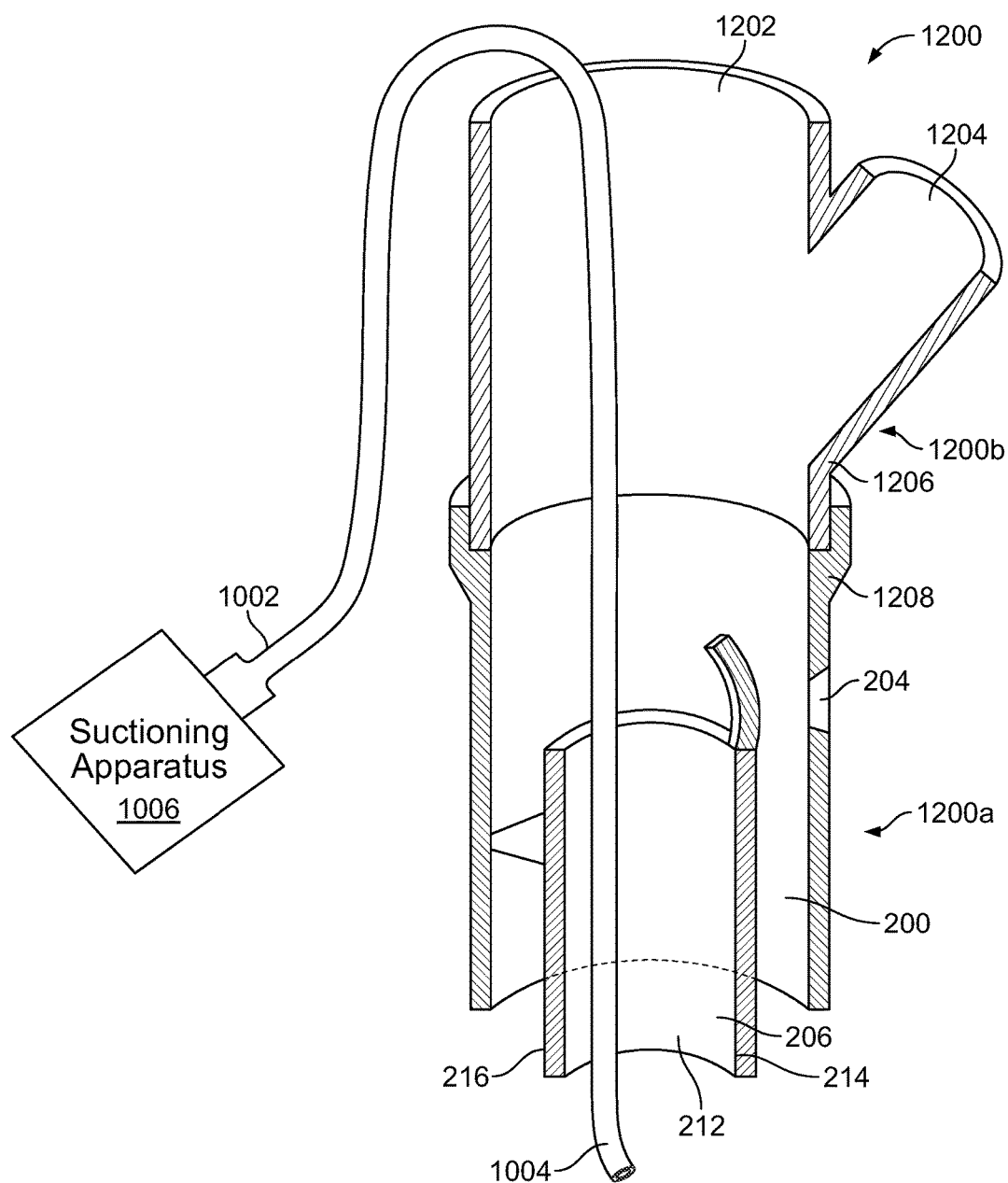
FIG. 12 is a fragmentary cross-sectional view of a tracheostomy tube adaptor device with a suction port for receiving a suction tube and a ventilation port for connecting to ventilation tubing.

FIG. 12 is a fragmentary cross-sectional view of a tracheostomy tube adaptor device 1200 with a suction port 1202 for receiving a suction tube 1000 and a ventilation port 1204 for connecting to ventilation tubing (not shown), according to certain embodiments. The tracheostomy tube adaptor 1200 includes a condensation adaptor 1200*a* and a suctioning adaptor 1200*b*. The upper end 1208 of the condensation adaptor 1200*a* connects to a lower end of the suctioning adapter 1200*b*. The connection may be secured by an interference fit, a snap fit, an adhesive, a weld, a fastener, or any suitable connection mechanism or combination thereof. Although the tracheostomy tube adaptor shown in FIG. 12 has two parts, in some embodiments, the adaptors 1200*a* and 1200*b* are integrally formed.

The presence of the two ports 1202 and 1204 allows suction tubing 1002 to be introduced through suction port 1202 into the tracheostomy tube of the patient to remove mucus secretions, while ventilation is continuously applied at ventilation port 1204 and/or breathing gas is applied at breathing gas port 204. Therefore, suctioning of the tracheostomy tube may be performed without disconnecting the patient from the source of breathing gas. In some implementations, the suction tubing 1000 is connected at suction port 1202, breathing gas is delivered through breathing gas port 204, and the ventilation port 1204 remains disconnected. In such implementations, the ventilation port 1204 functions as an exhaust port during exhalation or when the flow rate of breathing gas exceeds the rate of inspiration of the patient.

In some implementations, the ventilation port 1204 allows a patient to be connected to a mechanical ventilator while also receiving a high flow rate of heated and humidified breathing gas through breathing gas port 204. Such implementations may assist a patient transitioning from mechanical ventilation to a respiratory therapy, such as high flow therapy. For example, if a patient were to show signs of distress during a transition from mechanical ventilation to high flow therapy, the presence of ventilation port 1204 allows the patient to be quickly reconnected to ventilation without disconnecting high flow therapy. Similarly, a patient may be regularly alternated between being connected to one or both of mechanical ventilation and high flow therapy by a healthcare professional by simply connecting and disconnecting therapy at the ports and without disconnecting suction or changing the adaptor 1200.

Figure 13:
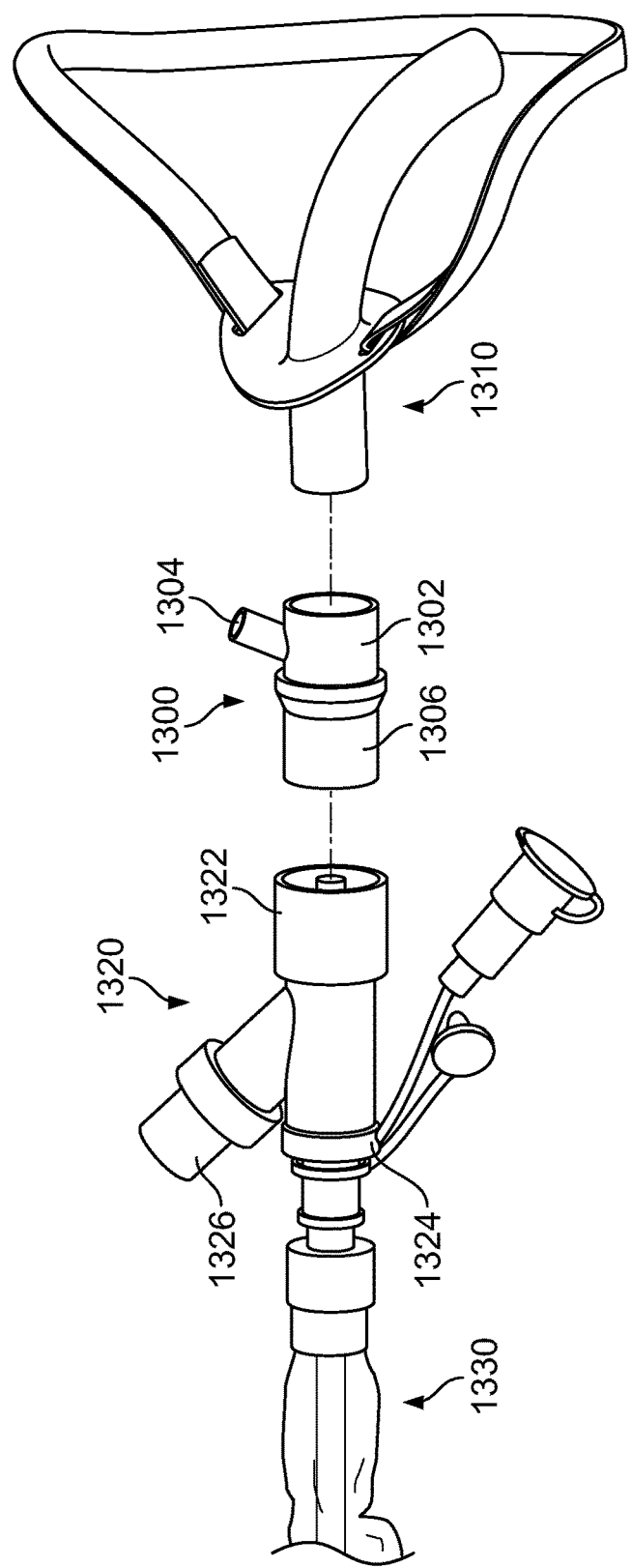
FIG. 13 is a perspective view of a tracheostomy tube adaptor device for receiving a suctioning catheter.

FIG. 13 is a perspective view of a tracheostomy tube adaptor device 1300 for receiving a suctioning catheter 1330, according to certain embodiments. The tracheostomy adaptor 1300 includes a tracheostomy tube port 1302 for connecting to a tracheostomy tube, a breathing gas port 1304 for coupling to a source of breathing gas, and a dual-purpose port 1306. Although ports 1304 and 1306 are shown in FIG. 12 in a single lumen configuration, in some implementations the ports may be configured as a dual lumen tube with an outer sleeve providing high flow heated and humidified gas into the tracheostomy tube and an inner lumen functioning as the breathing gas port. The breathing gas port 1304 may receive heated and humidified breathing gas at a high flow rate (e.g. 8 L/min-40 L/min). The breathing gas port 1304 may be aligned substantially perpendicular to the long axis of the tracheostomy tube adaptor device 1300, angled towards the tracheostomy tube port 1302, aligned in any other suitable orientation, or configured to be adjustable between any suitable orientations. If breathing gas is delivered through the breathing gas port 1304 when it is oriented perpendicularly, breathing gas may flow primarily out of the dual-purpose port 1306 instead of into tracheostomy tube port 1302. Breathing gas may be drawn through tracheostomy tube port 1302 primarily when the patient inhales. The flow of breathing gas out of the dual-purpose port 1306 in the perpendicular arrangement may facilitate rapid removal of carbon dioxide during exhalation. If breathing gas is delivered through the breathing gas port 1304 when it is angled towards the tracheostomy tube port, the majority of the breathing gas may flow into the tracheostomy tube. The increased flow of breathing gas into the tracheostomy tube in the angled arrangement relative to the perpendicular arrangement may provide extrinsic positive end expiratory pressure (PEEP), enhancing airway secretion clearance. PEEP may increase airway pressure, prevent airway collapse, and may increase the partial pressure of oxygen in arterial blood ($PaO_2$). PEEP may also increase recruitment of alveoli by preventing cyclic de-recruitment on expiration, decrease airway resistance, improve the distribution of inspired gas, reduce the patient's work of breathing, prevent surfactant aggregation reducing alveolar collapse, and reduce the left ventricular afterload.

The dual-purpose port 1306 connects to an adaptor 1320, such as the Verso™ adapter (CareFusion, San Diego, Calif.). The adaptor 1320 includes a tracheostomy tube port 1322, for coupling with the tracheostomy tube adaptor 1300, a ventilation port 1326 for coupling with a ventilator, and a suction port 1324 for receiving a suction catheter 1330. The suction catheter 1330 may be used to suction a patient's mobilized airway secretions to prevent the tracheostomy tube from clogging. A patient can be coupled to a source of ventilation, a source of high flow therapy, and a suctioning apparatus at once, and the tracheostomy tube adaptor 1300 may remain in place even while the combination of connections is changed. For example, the tracheostomy tube adaptor device 1300 can remain in place when a patient is switched between ventilation and high flow therapy. In certain implementations, the adaptor 1320 may include a built-in suction catheter.

Figure 14:
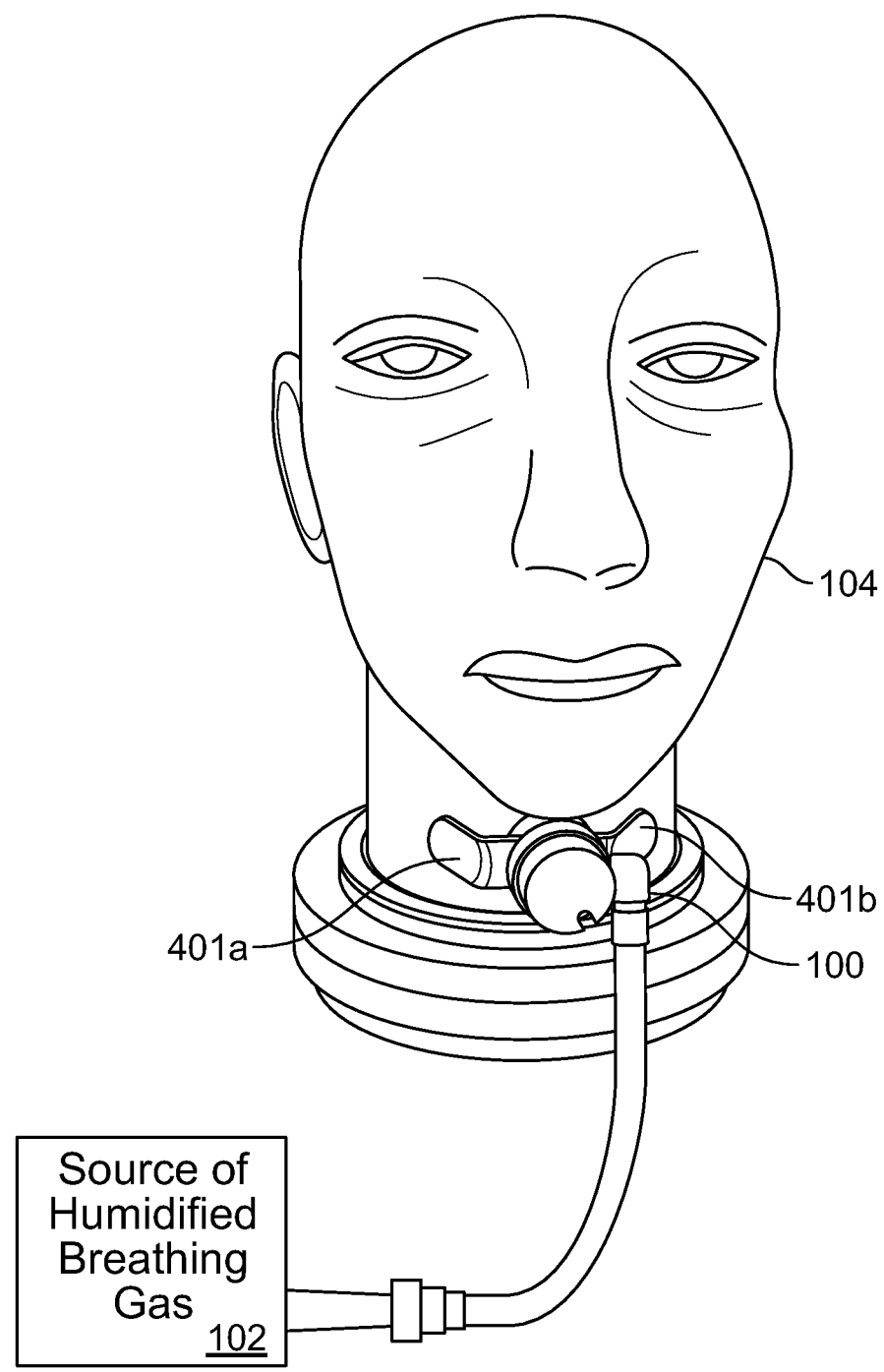
FIG. 14 is a perspective view of a tracheostomy tube adaptor device for coupling a tracheostomy tube with a source of humidified breathing gas.

FIG. 14 depicts the tracheostomy tube adaptor device 450 of FIG. 4 coupled to a tracheostomy tube protruding from a neck of a patient 104, according to certain embodiments. In use, the tracheostomy tube adaptor device 450 couples the source of humidified breathing gas 102 with the tracheostomy tube of the patient 104. The tracheostomy tube adaptor device 450 includes flanges 401a and 401b which engage the neck of the patient 104. As discussed in relation to FIG. 4, flanges 401a and 401b may connect to a tracheostomy band (not shown) circling the neck of the patient 104.

In use, with reference to FIGS. 1-14, humidified breathing gas from source 102 passes through tube 500 to adaptor 100. The humidified breathing gas passes through a breathing gas port 204 in the housing 200. The humidified breathing gas encounters a baffle 208 prior to passing through a breathing gas passage 222 of a tracheostomy tube connection device 206 for delivery to the tracheostomy tube of a patient. The baffle 208 disrupts the flow of the humidified breathing gas to induce condensation in a controlled manner. The induced condensation is channeled into a condensation passage 224.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in high flow therapy systems, may be applied to systems, devices, and methods to be used in other ventilation circuits.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. An adaptor for coupling a tracheostomy tube to a source of humidified breathing gas, the adaptor comprising:
    a housing having an interior surface, an exterior surface, and a breathing gas port for receiving a flow of humidified breathing gas from the source, the breathing gas port extending from the exterior surface to the interior surface;
    a tracheostomy tube connection device positioned within the housing, the tracheostomy tube connection device including an input port for receiving the flow of humidified breathing gas from the breathing gas port and an output port for coupling with the tracheostomy tube, the tracheostomy tube connection device having an internal surface defining a breathing gas passage and an external surface spaced from the interior surface of the housing to create a condensation passage wherein the condensation passage comprises a bottom end, and wherein the condensation passage is configured such that condensation flows towards the bottom end and exits the adaptor;
    a baffle positioned between the breathing gas port and the input port to cause controlled condensation from the flow of humidified breathing gas by disrupting the flow of humidified breathing gas; and
    at least one projection, positioned within the housing, to space the tracheostomy tube connection device from the interior surface of the housing.

2. The adaptor of claim 1, wherein the baffle is integrally formed with the tracheostomy tube connection device.

3. The adaptor of claim 1, wherein the external surface of the tracheostomy tube connection device includes the at least one projection.

4. The adaptor of claim 1, wherein the interior surface of the housing includes the at least one projection.

5. The adaptor of claim 1, wherein the adaptor further comprises at least one flange attached to the external surface of the tracheostomy tube connection device to prevent displacement of the tracheostomy tube and to distribute force if the tracheostomy tube connection device is moved.

6. The adaptor of claim 5, wherein the at least one flange has a surface configured to engage a neck of a patient, the surface having a connector to connect the at least one flange to a tracheostomy band circling the neck.

7. The adaptor of claim 6, wherein the connector is a hook or loop connector.

8. The adaptor of claim 1, wherein the adaptor further comprises at least one flange attached to the exterior surface of the housing to prevent displacement of the tracheostomy tube and to distribute force if the tracheostomy tube connection device is moved.

9. The adaptor of claim 1, wherein the adaptor further comprises:
a supply tube having a first end to receive the flow of humidified breathing gas and a second end coupled to the breathing gas port of the housing.

10. The adaptor of claim 9, further comprising:
a swivel connector coupled to the first end of the supply tube for connection with the source of humidified breathing gas.

11. The adaptor of claim 1, wherein the breathing gas port includes an elbow connector for coupling with the source of humidified breathing gas.

12. The adaptor of claim 1, wherein the breathing gas port includes a straight connector for coupling with the source of humidified breathing gas.

13. The adaptor of claim 1, wherein the output port of the tracheostomy tube connection device has an interior surface configured to engage an exterior surface of the tracheostomy tube.

14. The adaptor of claim 1, wherein the output port of the tracheostomy tube connection device has an exterior surface configured to engage an interior surface of the tracheostomy tube.

15. The adaptor of claim 1, wherein the external surface of the tracheostomy tube connection device has a first perimeter, the adaptor further comprising:
a vent cap coupled to the housing, the vent cap including an inner surface having a second perimeter;
wherein the first perimeter is smaller than the second perimeter such that condensate that accumulates on the vent cap flows into the condensation passage.

16. The adaptor of claim 15, wherein the vent cap is removably coupled to the housing.

17. The adaptor of claim 16, wherein the vent cap comprises:
a cap base for removably coupling with the housing;
a sloping planar structure coupled to the cap base to form at least one opening, the at least one opening capable of operating as a vent for exhaled air.

18. The adaptor of claim 17, wherein the at least one opening includes a first opening portion and a second opening portion, wherein the first opening portion is larger than the second opening portion due to a slope of the sloping planar structure, and the first opening portion is positioned opposite to the second opening portion with respect to the second perimeter.

19. The adaptor of claim 1, wherein the adaptor further comprises a tube sleeve configured to receive a suction tube to suction away secretions in the airway of a patient.

20. The adaptor of claim 19, further comprising the suction tube, the suction tube having a first tube end and a second tube end, the first tube end extending out of the adaptor for coupling with a suctioning apparatus and the second tube end extending into the airway of a patient to suction away secretions when positioned within the tube sleeve.

21. The adaptor of claim 20, wherein the tube sleeve is fixedly bonded to a surface of the tracheostomy tube connection device and the second tube end extends through the tube sleeve so as to be capable of extending into the airway of the patient.

22. The adaptor of claim 1, wherein the condensation passage is capable of serving as a vent for exhaled air.

23. The adaptor of claim 1, wherein the at least one projection is integrally formed with at least one of: the housing and tracheostomy tube connection device.

24. The adaptor of claim 1, wherein the bottom end of the condensation passage is located longitudinally opposite the input port.

25. The adaptor of claim 24, wherein the housing comprises an upper end and the bottom end of the condensation passage is located opposite of the upper end of the housing.

* * * * *